United States Patent [19]

Baker

[11] Patent Number: 5,045,536
[45] Date of Patent: Sep. 3, 1991

[54] LIQUID FORMULATIONS

[76] Inventor: Ivor P. Baker, Coopers Animal Health Limited, Berkhamsted Hill, Berkhamsted, Hertfordshire, England

[21] Appl. No.: 434,545

[22] Filed: Nov. 9, 1989

Related U.S. Application Data

[63] Continuation of Ser. No. 58,526, Jun. 5, 1987, abandoned.

[30] Foreign Application Priority Data

Jun. 7, 1986 [GB] United Kingdom ............... 8613914

[51] Int. Cl.$^5$ ..................... A01N 55/00; A01N 37/34
[52] U.S. Cl. ...................................... 514/63; 514/521; 514/531; 514/552; 424/DIG. 10
[58] Field of Search ............... 514/521, 552, 531, 772, 514/770, 63; 424/DIG. 18

[56] References Cited

U.S. PATENT DOCUMENTS

| | | |
|---|---|---|
| 2,988,473 | 6/1961 | Millis et al. |
| 4,212,897 | 7/1980 | Young et al. ..................... 427/2 |
| 4,672,072 | 6/1987 | Hackney et al. ................ 514/368 |

FOREIGN PATENT DOCUMENTS 0045424 10/1982 European Pat. Off.

*Primary Examiner*—John W. Rollins
*Attorney, Agent, or Firm*—Donald Brown

[57] ABSTRACT

A pour-on formulation comprising one or more ectoparasiticides in a solvent system comprising 80 to 98% w/v of a fixed oil and 2 to 20% w/v of a volatile silicone, a method for its preparations and its use in the control of ectoparasiticides on animals.

8 Claims, No Drawings

LIQUID FORMULATIONS

This is a continuation of copending application Ser. No. 07/058,526 filed on June 5, 1987, now abandoned.

The present invention relates to liquid formulations for localised topical application which contain substances having ectoparasiticidal activity and to methods of controlling parasites of animals by administration of such formulations.

Formulations for localised topical appliation, such as pour-on or spot-on formulations, are now well known in the art and are described, for example, in Australian Patent Application 73640/81 and UK Patent Application 8134831 (Publication No. 2088212). These formulations are applied topically to a limited area of the animal's body surface and the ectoparasiticide is believed to migrate over the body surface to control ectoparasites distant from the points of application.

Unfortunately, it has been discovered that a number of solvent systems described in the art provide formulations for localised topical application which cause irritancy or toxicity to the animal on administration. This is particularly the case with substances which are insoluble in a range of solvents, thereby restricting the choice of solvent that can be used to provide a pour-on formulation where the active substance is in solution.

It has now been found that a particular solvent system has the combined properties of low irritancy and appropriate solvency and is particularly suitable for use in formulations for localised topical application.

Accordingly, the present invention provides a pour-on formulation comprising one or more ectoparasiticides in a solvent system comprising 80 to 98% w/v of a fixed oil and 2 to 20% w/v of a volatile silicone.

When used herein, the term "fixed oil" refers to non-volatile oils which are lipids extracted from plants and animals. They are composed mainly of esters of glycerol and higher fatty acids. Examples of fixed oils include arachis, castor, maize, olive, rape and soya oils.

Suitably the fixed oil is dewaxed. Preferably the fixed oil is maize oil.

Maize oil is a mixture of triglycerides of fatty acids (see for example The Merck Index, 9th Ed., 2510).

Volatile silicones are cyclic dialkylpolysiloxanes (see for example The Merck Index, 9th Ed., 8237).

Preferred volatile silicones include dimethylpolysiloxanes such as V5-7158 marketed by the Union Carbide Corporation, Danbury, Conn. U.S.A.

Suitably the solvent system comprises 88 to 98% w/v maize oil and 2 to 12% w/v volatile silicone.

The present formulations may contain up to 18% w/v of additives conveniently used in pour-on formulations, for example spreading agents, synergists, attractants, repellents, adhesion promoters, surface active agents, stabilisers and colouring agents. Suitably the formulations of the present invention contain up to 10% w/v of such additives and preferably below 5% w/v of such additives.

In one preferred embodiment the formulations of the present invention will include less than 1% w/v of additives. Preferably the formulations will contain no additives, or colouring agents are the only additives included and these will be present at a level of 0.5% or less.

Suitable spreading agents are liquids which distribute themselves particularly readily on the skin. Dowanol DPM (dipropylene glycol mono methyl ether) is a particularly suitable spreading agent for inclusion within the formulations of the present invention. Isopropyl myristate is another commonly used spreading agent. Australian Patent Application 73640/81 describes the properties of spreading agents (referred to as spreading oils) and lists various classes of these substances.

Attractants include pheromones such as 2,6-dichlorophenol. Repellents include citronellol, diethyl toluimide, dimethyl phthalate, and the like.

Adhesion promoters include carboxymethylcellulose, methylcellulose and other cellulose derivatives and starch derivatives, polyacrylates, alginates, gelatin, gum arabic, polyvinylpyrrolidone, polyvinyl alcohol, copolymers of methyl vinyl ether and maleic anhydride, polyethylene glycols, paraffins, oils, waxes and hydrogenated castor oil, colloidal silicic acid or mixtures of the substances mentioned.

The formulations of the present invention do not normally contain surface active agents; however these may be included if desired.

Surface-active agents (comprising emulsifiers and wetting agents) include:

1. anionic surface-active agents, such as Na lauryl sulphate, fatty alcohol ether-sulphates and monoethanolamine salts of mono-/di-alkylpolyglycol ether orthophosphoric acid esters, 2. cationic surface-active agents, such as cetyltrimethylammonium chloride, 3. ampholytic surface-active agents, such as di-Na-N-lauryl- aminodipropionate or lecithin, and 4. non-ionic surface-active agents, for example, polyoxyethylated castor oil, polyoxyethylated sorbitane monooleate, sorbitan monostearate, ethyl alcohol, glycerol monosterate, polyoxyethylene stearate and alkylphenol polyglycol ethers.

Stabilisers for preventing the chemical degradation which occurs in the case of some active compounds include, for example, antioxidants, such as tocopherols, butylhydroxyanisole, butylhydroxytoluene and carbodiimides, e.g. Stabaxol (2,2$^1$,6,6$^1$-tetraisopropyldiphenyl- carbodiimide) and scavengers such as epichlorhydrin. Colouring agents include conventional dyes which are soluble in the carrier of the present invention, such as Sudan Red or Oil Golden Yellow.

The ectoparasiticide incorporated within a formulation of the present invention may be active against one or more ectoparasite species including insects and acarines, including lice, ticks, keds, mites, fleas and flies.

Water insoluble ectoparasiticides agents are particularly suitable for inclusion in the present invention and include pyrethrins, pyrethroids, carbamates, water-insoluble organo-phosphorus compounds, benzoyl ureas, formamidines, triazines, avermectins (or milbemycins) other standard ectoparasitides and mixtures thereof. Suitable milbemycins are disclosed in Australian published patent applications numbers 42309/78 and 42389/78. Where there are isomers of ectoparasiticides, both the ectoparasitically active isomers themselves and mixtures thereof with non-ectoparasitically active isomers are suitable for inclusion within the formulations of the present invention.

Preferred pyrethroids have the formula

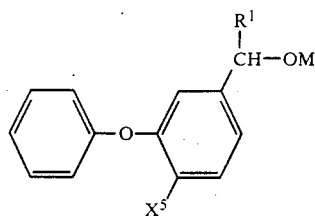

wherein M is

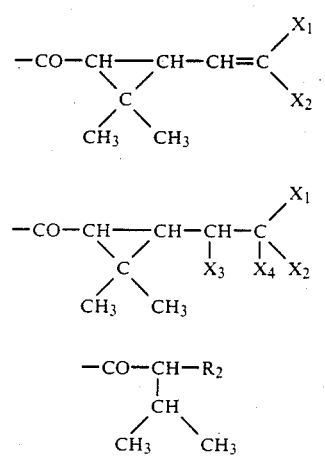

and wherein
X₁ to X₄ are independently selected from halo C₁–C₄ alkyl, halogen-substituted C₁–C₄ alkyl, and halogen-substituted phenyl;

$X_5$ is —H or halo;

$R_1$ is —H or cyano; and $R_2$ is phenyl substituted by halogen or halogen-substituted C₁₋₄ alkoxy, or $R^2$ is anilino substituted by halogen and/or halogen-substituted C₁₋₄ alkyl.

Particularly preferred compounds are presented in Tables I to III.

TABLE I $$M = -CO-CH-CH-CH=C\begin{matrix}X_1\\X_2\end{matrix}$$
$$\quad\quad\quad\; \backslash C / $$
$$\quad\quad CH_3\; CH_3$$

| No. | X₁ | X₂ | X₃ | X₄ | X₅ | R₁ | trivial name |
|---|---|---|---|---|---|---|---|
| 1 | Cl | Cl | — | — | H | H | permethrin |
| 2 | CH₃ | CH₃ | — | — | H | H | phenothrin |
| 3 | Br | Br | — | — | H | CN | deltamethrin |
| 4 | Cl | Cl | — | — | H | CN | cypermethrin |
| 5 | Cl | CF₃ | — | — | H | CN | cyhalothrin |
| 6 | Cl-⌬- | Cl | — | — | F | CN | flumethrin |
| 7 | Cl | Cl | — | — | F | CN | cyfluthrin |
| 8 | CH₃ | CH₃ | — | — | H | CN | cyphenothrin |

TABLE II $$M = -CO-CH-CH-CH-C\begin{matrix}X_1\\X_3\; X_4\; X_2\end{matrix}$$

| No. | X₁ | X₂ | X₃ | X₄ | X₅ | R₁ | trivial name |
|---|---|---|---|---|---|---|---|
| 9 | Br | Br | Br | Br | H | CN | tralomethrin |
| 10 | Cl | Cl | Br | Br | H | CN | tralocythrin |

TABLE III $$M = -CO-CH-R_2$$
$$\quad\quad\; |$$
$$\quad\quad CH$$
$$\quad CH_3\; CH_3$$

| No. | R₂ | X₅ | R₁ | trivial name |
|---|---|---|---|---|
| 11 | —⌬—Cl | H | CN | fenvalerate |
| 12 | —⌬—OCHF₂ | H | CN | flucythrinate |
| 13 | —⌬(Cl)—CF₃ | H | CN | fluvalinate |

Deltamethrin, cypermethrin, permethrin, flumethrin, cyhalothrin and alphamethrin are particularly suitable pyrethroids for inclusion within the formulations of the invention. Alphamethrin is a 1:1 mixture of the 1R-cis S and 1S-cis R isomers of α-cyano-3-phenoxybenzyl-2,2-dimethyl-3-(2,2-dichlorovinyl)-cyclopropanecarboxylate. Cyhalothrin or an individual isomer or mixture of isomers thereof is a particularly preferred pyrethroid.

Preferred carbamates include carbaryl and promacyl.

Preferred water-insoluble organophosphorus compounds include the following:

O-2-diethylamino-6-methylpyrimidin-4-yl O,O-diethyl phosphorothioate (pirmiphos-ethyl)

O-2-diethylamino-6-methylprimidin-4-yl O,O-dimethyl phosphorothioate (pirimiphos-methyl)

O-(4-bromo-2,5-dichlorophenyl)O,O-diethyl phosphorothioate (bromophos-ethyl)

2-chloro-1-(2,4-dichlorophenyl) vinyl diethyl phosphate (chlorfenvinphos)

O,O-diethyl O-(3,5,6-trichloro-2-pyridyl)phosphorothioate (chlorpyrifos)

O,O-diethyl-O-(3-chloro-4-methyl-7-coumarinyl)phosphorothioate (coumaphos);

O,O-diethyl-O-(2-isopropyl-6-methyl-pyrimidin-4-yl)phosphorothioate (diazinon);

O-2,4-dichlorophenyl O,O-diethylphosphorothioate (dichlofenthion)

2,3-p-dioxanedithiol S,S-bis, O,O-diethyl phosphorodithioate (dioxathion);

O-ethyl-O-(quinol-8-yl)phenylphosphorothioate (oxinothiophos);

O,O,O,O,-tetraethyl S,S'-methylene di(phosphorodithioate) (ethion)

O,O-dimethyl-O-2,4,5-trichlorophenyl phosphorothioate (fenchlorphos);

O,O-dimethyl-O-(4-dimethylsulfamoylphenyl)phosphorothioate (famphur);

O,O-dimethyl-O-(4-nitro-m-tolyl)phosphorothioate (fenitrothion);

O,O-diethyl-O-cyanobenzylideneamino-oxyphosphonothioate (phoxim); and (E)-O-2-iospropoxycarbonyl-1-methylvinyl O-methyl ethylphosphoramidothioate (propetamphos)

Preferred formamidines include water-insoluble compounds of the formula

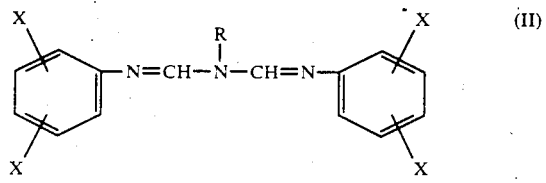

wherein R is hydrogen or $C_{1-6}$ alkyl, and each X is independently selected from hydrogen, $C_{1-6}$ alkyl and halo.

Particularly preferred formamidines include N,N-di-(2,4-xylyliminomethyl)methylamine (called amitraz).

Preferred triazines include cyromazine.

When a pyrethroid is included in a formulation of the present invention it will suitably be present at a concentration of 10% w/v or less. Cyhalothrin will suitably be present at a concentration from 0.1 to 5%, preferably 1 to 3% and conveniently 2%.

Other active substances, as hereinbefore defined, will suitably be present at a concentration of less than 50%, suitably less than 30%, for example between 1 and 15%. Normally, there will be a maximum of three active substances in the formulation and preferably only one. Preferred mixtures of active substances include a pyrethroid with a second pyrethroid, with a water insoluble organophosphorus compound, for example pirimiphos methyl, with a formamidine, for example amitraz, or with a carbamate, for example promacyl.

Alternatively the ectoparasiticide may be combined in a formulation of the present invention with an anthelmintic, for example a thiazole such as levamisole. The combination of permethrin and levamisole in a solvent system comprising 80-98% w/v of maize oil and 2 to 20% w/v of a volatile silicone is an example of such a formulation.

The invention in a second aspect provides a method of controlling external parasites which comprises making a localised external application of a formulation as hereinbefore defined to an animal. External parasites include those of the Classes Arachnida (especially acarines) and Insecta (especially Phthiraptera and Diptera). External parasites of particular commercial significance include:

Sheep: *Melophagus ovinus*—ked, *Damalinia ovis*—biting louse, *Linognathus ovillus*—sucking louse, *L. pedalis*—sucking louse, *Lucilia* spp.—blowfly, *Culicoides* spp—midges, *Hydrotaea irritans*—headfly, *Oestrus ovis*—nasal botfly, *Psoroptes ovis*—sheep scab, *Psorergates ovis*—sheep itchmite, *Ixodes ricinus*, *Rhipicephalus* spp, *Amblyomma* spp, *Haemaphysalis* spp.

Goats: *Damalinia caprae*—biting louse, *D. limbata*—biting louse, *D. crassipes*—biting louse, *Linognathus stenopsis*—sucking louse, Cattle:
a) Lice *Damalinia bovis*—biting louse, *Linognathus vituli*—sucking louse, *Haematopinus eurysternus*—sucking louse, *Solenopotes capillatus*—sucking louse
b) Flies *Musca domestica*, *M. autumnalis*, *Stomoxys calcitrans*, *Lyperosia irritans*, *Haematobia thirouxi potans*, *H. exigua*, *Simulium* spp., *Glossina* spp, *Dermatobia Lominus*, *Hydrotaea irritans*, Tabanids, *Hypoderma* spp.
c) Ticks *Boophilus microplus*, *B. decoloratus*, *Rhipicephalus appendiculatus*, *R. evertsi*, *Amblyomma hebraeum*, *A. variegatum*, *Hyalomma rufipes*, *H. truncatum*, *Haemaphysalis longicornis*, *Dermacenter* spp, *Ixodes* spp, *Otobius megnini*, *Ornithodorus savignyi*.

Horses:
a) Flies *Musca* spp, *Stomoxys calcitrans*, Tabanids
b) Lice *Damalania equi*, *Haematopinus asini*
c) Mange *Sarcoptes scabiei* var equi Pigs: *Sarcoptes scabiei* var suis—mange, *Haematopinus suis*—sucking louse Dog: *Linognathus setosus*—sucking louse, *Trichodectes canis*—biting louse, *Ctenocephalides canis*—flea, *Rhipicephalus sanguineus*—tick, *Haemaphysalis leachii*—tick, *Demodex canis*, *Otodectes cynotis*, *Sarcoptes scabiei* var canis—manges.

Cat: *Notoedrisati*—face mange, *Otodectes cynotis*—ear mange *Ctenocephalides felis*—cat flea, *Ixodes* spp—tick, *Felicola subrostrata*—louse.

Fur bearing animals: *Otodectes cynotis*—mites of mustelids:

Poultry:
a) Ticks *Argas persicus*
b) Mites *Ornithonyssus sylviarum*, *Dermanyssus gallinae*

Lice: *Menopon gallinae*, *Menacanthus stramineus*.

The animal is preferably a mammal, and may be selected from cattle, goats, pigs, horses, deer, sheep, fur bearing animals such as mink, rabbits and domestic pets such as cats and dogs. The animal may also be a bird, e.g. selected from ducks, chickens and geese. Suitably the animal is selected from cattle, sheep, pigs and dogs. Preferably the formulations of the present invention will be used to treat lice and keds on sheep and goats and lice, flies and ticks on cattle.

The pour-on formulation may be applied to the animal by any conventional method for the localised application of formulations, for example by wiping an impregnated material over a small area of the animal's body or by the use of commercially available applicators, such as the Clout Backliner Applicator (Registered Trademark) or a pump dispenser or a roll-on or by the apparatus described in Australian Patent No. 494198. Generally, the pour-on formulation is applied by pouring in one or several lines or in a spot on the back or shoulder or other parasite predilection sites of the animal. Alternatively, it may be applied by means of a localised spray.

It is a particular advantage of the use of pour-on formulations that only small volumes of the formulation need to be applied. Depending on the size of the animal, the volume applied will generally lie in the range 2-60 ml, and suitably 5-30 ml for larger mammals. The amount of active substance, as hereinbefore defined, administered to an animal will depend on the size of the animal, the amount can be between 10 mg and 10 g but will normally be between 10 mg and 1 g. Preferably 50 to 200 mg of active substance will be applied to a sheep and 100 to 600 mg of active substance will be applied to a cow.

The formulations of the present invention will be prepared by standard techniques, i.e. in the case where the formulation is a solution by bringing the ectoparasiticide into contact with the solvent system and then gently heating and stirring until dissolved if necessary. If the ectoparasiticide is insoluble in or immiscible with the carrier then a suspension, dispersion or emulsion may be prepared by standard techniques. To prepare a suspension the ectoparasiticide may be ground in the carrier to the required particle size and the remaining excipients added with stirring until the final product is of uniform consistency; generally heating is not necessary. To prepare a dispersion or emulsion, the ectoparasiticide is dissolved in the carrier together with a suitable emulsifier and then admixed with the water or other immicible vehicle. The whole is homogenised by conventional means. Emulsions, dispersions and suspensions are not preferred formulations of the present invention.

Preferred formulations will now be described by way of example only as follows:

GENERAL PROCEDURE FOR PREPARING FORMULATIONS

General Preparation

In the case of a solid the active ingredient (for example deltamethrin) is added to the solvent with stirring. Gentle heat is applied, where necessary, and stirring is continued until all the solid has dissolved and a homogenous mixture obtained. Auxiliaries to be included in the formulation may be either mixed with the active ingredient before addition of the solvent or added to the homogenous mixture of active ingredient and solvent.

Combinations of active ingredients will be prepared in the same manner as formulations of single active ingredients.

In the case where the active ingredient(s) is a liquid (e.g. supona), then the preparation is prepared by mixing the two (or more) liquids together until the product is homogeneous. Heat will not generally be necessary.

Example 1 a) Cyhalothrin technical (88%) — 2.25 g
Volatile Silicone VS 7158 — 4.65 g
Dewaxed Maize Oil (Croda, Hull, England) to — 100 ml
b) Cyhalothrin technical (88%) — 2.25 g
Volatile Silicone VS 7158 — 9.30 g
Dewaxed Maize Oil (Croda) to — 100 ml
c) Cyhalothrin technical (88%) — 2.25 g
Volatile Silicone VS 7158 — 4.65 g
Butylhydroxyanisole — 0.0465 g
Dewaxed Maize Oil (Croda) to — 100 ml

Example 2

Cyhalothrin technical (88%) — 1.2 g
Amitraz technical (99%) — 5.0 g
Volatile Silicone VS 7158 — 4.65 g
Stabaxol — 0.46 g
Dewaxed Maize Oil (Croda) to — 100 ml

Example 3 a) Amitraz technical (99%) — 5.0 g
Volatile Silicone VS 7158 — 4.65 g
Stabaxol — 0.46 g
Dewaxed Maize Oil (Croda) to — 100 ml
b) Deltamethrin Technical (98.5%) — 2.02 g
Volatile Silicone VS7158 — 4.65 g
Dewaxed Maize Oil (Croda) to — 100 ml
c) Pirimiphos-ethyl Technical (95.6%) — 2.09 g
Volatile Silicone VS7158 — 4.65 g
Dewaxed Maize Oil (Croda) to — 100 ml
d) Pirimiphos-methyl Technical (91.5%) — 2.19 g
Volatile Silicone VS7158 — 4.65 g
Dewaxed Maize Oil (Croda) to — 100 ml
e) Diazinon Technical — 2.00 g
Volatile Silicone VS7158 — 4.65 g
Dewaxed Maize Oil (Croda) to — 100 ml
f) Supona Technical (90.7%) — 2.20 g
Volatile Silicone VS7158 — 4.65 g
Dewaxed Maize Oil (Croda) to — 100 ml
g) Cypermethrin Technical — 2.00 g
Volatile Silicone VS7158 — 4.65 g
Dewaxed Maize Oil (Croda) to — 100 ml
h) Deltamethrin Technical (98.5%) — 1.02 g
Volatile Silicone VS7158 — 4.65 g
Dewaxed Maize Oil (Croda) to — 100 ml
i) Deltamethrin Technical (98.5%) — 0.51 g
Volatile Silicone VS7158 — 4.65 g
Dewaxed Maize Oil (Croda) to — 100 ml
j) Flumethrin Technical (95%) — 1.05 g
Volatile Silicone VS7158 — 4.65 g
Dewaxed Maize Oil (Croda) to — 100 ml

Example 4 a) Cyhalothrin Technical (88%) — 2.25 g
Volatile Silicone VS7158 — 4.65 g
Dewaxed Sunflower Oil (Cargill UK) to — 100 ml
b) Cyhalothrin Technical (88%) — 2.25 g
Volatile Silicone VS7158 — 4.65 g
Rape Oil (Cargill UK) to — 100 ml
c) Cyhalothrin Technical (88%) — 2.25 g
Volatile Silicone VS7158 — 4.65 g
Dewaxed Soyabean Oil (Cargill UK) to — 100 ml
d) Cyhalothrin Technical — 2.25 g
Volatile Silicone VS7158 — 4.65 g
Groundnut (Arachis) Oil (Chambers and Fargo) to — 100 ml
e) Cyhalothrin Technical — 2.25 g
Volatile Silicone VS7158 — 4.65 g
Olive Oil (Andrew Steven Ltd.) to — 100 ml
f) Cyhalothrin Technical — 2.25 g
Volatile Silicone VS7158 — 4.65 g
Castor Oil, No. 1 grade (Croda) to — 100 ml
g) Cyhalothrin Technical — 2.25 g
Volatile Silicone VS7158 — 4.65 g
Castor Oil, commercial grade (Croda) to — 100 ml

I claim:

1. A pour-on formulation comprising one or more ectoparasiticides in a solvent system comprising 80 to 98% w/v of a fixed oil and 2 to 20% w/v of a volatile silicone.

2. A pour-on formulation according to claim 1 wherein the fixed oil is selected from arachis, castor, maize, olive, rape and soya oils.

3. A pour-on formulation according to claim 1 wherein the solvent system comprises 88 to 98% w/v maize oil and 2 to 12% w/v volatile silicone.

4. A pour-on formulation according to any one of claims 1 to 3 wherein the ectoparasiticides are selected from pyrethrins, pyrethroids, carbamates, water-insoluble organo-phosphorous compounds, benzoyl ureas, formamidines, triazines, avermectins and milbemycins.

5. A pour-on formulation according to any one of claims 1 to 3 wherein the ectoparasiticides are selected from deltamethrin, cypermethrin, permethrin, flumethrin, cyhalothrin, alphamethrin, amitraz, pirimiphos methyl and promacyl.

6. A method for the control of external parasites on animals which comprises making a localised external application of a pour-on formulation according to any one of claims 1 to 3 to the animal.

7. A pour-on formulation according to any one of claims 1 to 3 for use in the control of external parasites on animals.

8. A method for the preparation of a pour-on formulation according to any one of claims 1 to 3 which comprises bringing the ectoparasiticide into contact with the solvent system and thereafter mixing and/or gently heating if required.

* * * * *